United States Patent
Zhu et al.

(10) Patent No.: US 8,161,904 B2
(45) Date of Patent: Apr. 24, 2012

(54) DIRECT COATING SOLID DOSAGE FORMS USING POWDERED MATERIALS

(75) Inventors: Jiangxu Zhu, London (CA); Yanfeng Luo, London (CA); Ying Liang Ma, London (CA); Hui Zhang, London (CA)

(73) Assignee: The University of Western Ontario, London, ON (CA)

( * ) Notice: Subject to any disclaimer, the term of this patent is extended or adjusted under 35 U.S.C. 154(b) by 18 days.

(21) Appl. No.: 12/946,644

(22) Filed: Nov. 15, 2010

(65) Prior Publication Data

US 2011/0114019 A1 May 19, 2011

Related U.S. Application Data

(62) Division of application No. 11/498,259, filed on Aug. 3, 2006, now Pat. No. 7,862,848.

(60) Provisional application No. 60/704,906, filed on Aug. 3, 2005.

(51) Int. Cl.
*B05C 5/02* (2006.01)

(52) U.S. Cl. ......... 118/627; 241/284; 118/19; 118/418; 424/497; 424/93.7; 427/2.14

(58) Field of Classification Search ............... 424/93.7, 424/497, 480, 482, 490, 494; 427/2.14, 2.18, 427/471, 485, 202, 212, 322, 346, 348, 536, 427/402, 407.1; 118/627
See application file for complete search history.

(56) References Cited

U.S. PATENT DOCUMENTS

| 4,640,218 | A | 2/1987 | Motoyama et al. |
| 5,470,603 | A * | 11/1995 | Staniforth et al. ........... 427/2.14 |
| 6,372,246 | B1 | 4/2002 | Wei et al. |
| 6,558,665 | B1 * | 5/2003 | Cohen et al. ................. 424/93.7 |
| 6,569,462 | B1 * | 5/2003 | Cornelli et al. ............... 424/497 |
| 2002/0034592 | A1 | 3/2002 | Hogan et al. |
| 2002/0197388 | A1 | 12/2002 | Brown et al. |
| 2003/0138487 | A1 | 7/2003 | Hogan et al. |
| 2003/0211229 | A1 | 11/2003 | Reeves et al. |
| 2004/0179322 | A1 | 9/2004 | Pletcher et al. |

FOREIGN PATENT DOCUMENTS

EP 0148772 7/1985
WO 97/29848 8/1997

OTHER PUBLICATIONS

Cerea et al., A novel powder coating process for attaining taste masking and moisture protective films applied to tablets, International Journal of Pharmaceutics, vol. 279, Issues 1-2, Jul. 26, 2004, pp. 127-139.

(Continued)

*Primary Examiner* — Dah-Wei Yuan
*Assistant Examiner* — Andrew Bowman
(74) *Attorney, Agent, or Firm* — Lynn C. Schumacher; Hill & Schumacher

(57) ABSTRACT

The present invention provides a method and apparatus for dry coating solid dosage forms. The method includes the steps of placing solid dosage forms in a rotatable, electrically grounded housing, and spraying a film forming polymer powder composition into the housing during rotation thereof to form a polymer coating on the solid dosage forms, the polymer powder composition being sprayed using an electrostatic spray gun, and curing the coated solid dosage forms.

22 Claims, 5 Drawing Sheets

OTHER PUBLICATIONS

Pearnchob et al., "Coating of pellets with micronized ethylcellulose particles by a dry powder coating technique", International Journal of Pharmaceutics, vol. 268, Issues 1-2, Dec. 11, 2003, pp. 1-11.

Pearnchob et al., "Dry Powder Coating of Pellets with Micronized Eudragit® RS for Extended Drug Release", Pharmaceutical Research, vol. 20, No. 12, pp. 1970-1976.

Pearnchob et al., "Dry polymer powder coating and comparison with conventional liquid-based coatings for Eudragit® RS, ethylcellulose and shellac", European Journal of Pharmaceutics and Biopharmaceutics, vol. 56, Issue 3, Nov. 2003, pp. 363-369.

Obara et al., "Dry coating: an innovative enteric coating method using a cellulose derivative", European Journal of Pharmaceutics and Biopharmaceutics, vol. 47, Issue 1, Jan. 1999, pp. 51-59.

* cited by examiner

DIRECT COATING SOLID DOSAGE FORMS USING POWDERED MATERIALS

CROSS REFERENCE TO RELATED U.S. APPLICATIONS

This patent application is a Divisional application of U.S. patent application Ser. No. 11/498,259 filed on Aug. 3, 2006 now U.S. Pat. No. 7,862,848 which relates to, and claims the priority benefit from, U.S. Provisional Patent Application Ser. No. 60/704,906 filed on Aug. 3, 2005, in English, entitled DIRECT COATING SOLID DOSAGE FORMS USING POWDERED MATERIALS, all of which are incorporated herein by reference in their entirety.

FIELD OF THE INVENTION

The present invention relates to a method and apparatus for dry coating solid dosage forms using powdered materials.

BACKGROUND OF THE INVENTION

Typically in the drug industry, drug products exist in two dosage forms, solid and liquid dosage forms. Included in the solid dosage forms are tablets, pellets, pills, beads, spherules and so on. These solid dosage forms are often coated for various reasons, such as odour or taste masking, protection from moisture, light and/or air, prevention from destruction by gastric acid or gastric enzymes, enhanced mechanical strength, aesthetics and controlled release including controlling release sites and/or release rate.

At present, the commercially used technology for coating solid dosage forms is the liquid coating technology. Generally, a mixture of polymers, pigments and excipients is dissolved in an appropriate organic solvent (for water insoluble polymers) or water (for water soluble polymers) to form a solution, or dispersed in water to form a dispersion, and then sprayed onto the dosage forms and dried by continuously providing heat, typically using hot air, until a dry coating film is formed.

The liquid coating processes and equipment have been well established and widely adopted by the pharmaceutical industry. Typical liquid coating is carried out in a rotary pan coater for larger size solid dosages such as tablets, or in a fluidized bed coater for smaller size dosage forms such as pellets or pills.

The liquid coating technique can give an exceptionally uniform smooth lustrous coating surface. However, the inherent disadvantages caused by using organic solvents or water have become increasingly obvious and unacceptable by the pharmaceutical industry. These include vaporizing organic solvents or water which is extremely energy consumptive. This adds considerable cost to the coating cost and long processing time is unavoidable.

In order to obtain a uniform smooth coating surface, temperature is regulated to prevent too fast a vaporizing rate which leads to formation of large pores. Furthermore, liquid coating feed rate needs also to be controlled to allow evaporation of the sprayed liquid so that the tablets do not become soaked in the liquid. The liquid spray cannot be too fast, to allow the evaporation of the sprayed liquid. If too much liquid is sprayed (than can be evaporated, the whole thing may become soaked. Therefore long processing time up to hours and even days is necessary for liquid coating to dry. Using organic solvents results in environmental pollution, solvent recycling cost and operation dangers of explosion.

Organic solvents add another cost to the coating cost in addition to the huge energy consumption and long processing time. From the viewpoint of cost and environment, usage of water in place of organic solvents is highly beneficial. However, evaporation of water still needs longer processing time and consumes much energy. In addition, enormous amount of hot air, especially in the case of a fluidized bed coater, is required to maintain the temperature of the coater and entrain the vapours out of the system. Because all air must be cleaned before and after the coater, the air treatment system adds significant cost to the entire system.

In order to overcome these limitations of liquid coating, new efforts have been made in recent years to develop a new technology based on powder coating, which is often termed as "dry coating" in the pharmaceutical coating fields.

The basics of dry coating include spraying of a mixture of finely ground particles of polymer and other materials onto the solid dosage surface without using any solvent, and then heating the dosages in a curing oven until the coating powder mixture is fused into a coating film on the dosage surface. Compared with traditional liquid coating, dry coating is highly valued for energy and time saving, high utilization of the coating material, long storage duration, environmental friendliness, safety, thereby resulting in low overall operation costs. To date, three dry coating processes have been developed in this area of technology. However, they are seen to have various shortcomings which limit them from becoming commercialized.

The first prior-art dry coating technique is based on the usage of plasticizers. This technique will be referred to as "plasticizer-dry-coating". Plasticizers, the majority of which are liquid organic chemicals with small molecular weight, are often added to lower the softening temperature ($T_s$) or glass transition temperature ($T_g$) of thermoplastic polymers, allowing film formation at a reduced temperature and improving the flexibility and tensile strength of the obtained film. The plasticizer is retained within the polymer and attenuates the attractive forces between the polymer chains to give flexibility during the whole life of the film. $T_s$ or $T_g$ decreases with the increase of plasticizer/polymer ratio. When plasticizer/polymer ratio is increased to an extent that the reduced $T_s$ or $T_g$ is close to or below the room temperature, the polymer film will become sticky and soft, having no practical values.

For solid dosage coating, low $T_s$ or $T_g$ of the film-forming polymer is essential to protect active ingredients in the dosages from being damaged at a high temperature which necessitates the use of plasticizers. In the prior-art plasticizer-dry-coating technique, powdered materials are sprayed onto a dosage surface simultaneously with spraying the plasticizer. The sprayed liquid plasticizer would wet the powdered particles and the dosage surface, promoting the adhesion of the particles to the dosage surface. Both the powder materials and plasticizer are sprayed by means of compressed air through separate nozzles. The coated dosages are then cured in an oven for a predetermined time above $T_g$ or $T_s$ of the polymer, forming a continuous film.

There are several prior arts mainly from two groups that reported the plasticizer-dry-coating. One group, Pearnchob et al., coated pellets with micronized ethylcellulose particles, Eudragit RS particles (a copolymer of methacrylic acid ester and trimethylammonioethyl methacrylate chloride) and shellac in a fluidized bed by means of the plasticizer-dry-coating technique (Pearnchob N, Bodmeier R. "Coating of pellets with micronized ethylcellulose particles by a dry powder coating technique", *International J Pharmaceutics,* 2003, 268:1-11; Pearnchob N, Bodmeier R. "Dry powder coating of pellets with micronized Eudragit RS for extended drug release", *Pharmaceutical Research*, 2003, 20: 1970-1976; Pearnchob N, Bodmeier R. "Dry polymer powder coating and comparison with conventional liquid-based coatings for Eudragit RS, ethylcellulose and shellac", *European J Pharmaceutics and Biopharmaceutics*, 2003, 56:363-369). The other group, Obara et al., used the same technique to coat tablets in a pan coater and beads in a fluidized bed with hydroxypropyl methylcellulose acetate succinate (HPMCAS) (Obara S, Maruyama N, Nishiyama Y, et al. "Dry coating: an innovative enteric coating method using a cellulose derivative", *European J Pharmaceutics and Biopharmaceutics*, 1999, 47: 51-59).

FIG. 1 is a schematic diagram of a Prior-Art electrostatic coating apparatus for solid dosage forms wherein disclosed in US 2002/0034592 A1 in which 10 is a tablet feeding chute; 12. 12' are rotary drums; 16, 16' are electrostatic spraying guns; 18, 18' are trays to hold particles; 20, 20' are infrared ray heaters; 22: tablet collection chutes; A (A') are preconditioning stations; B (B') are coating stations; C (C') are fusing stations.

FIG. 2 is a schematic diagram of a Prior-Art heat-dry-coating apparatus and process for tablet coating disclosed by Cerea M et al. wherein (1) rotating disk; (2) infrared lamp; (3) powder feeder; (4) temperature probe; (5) coating tablets; (6) glass cover.

The effects of plasticizer types and concentration and curing temperatures on the film forming ability of polymers, surface morphology and controlled release profiles of the obtained coats have been investigated in some of the above listed references. Both Pearnchob and Obara indicated that the coating thickness or coating level (coating level is referred to as the weight gain based on the uncoated dosage weight) could be regulated by the amount of plasticizer feeding, a much larger amount of plasticizer being required for the adhesion of more particles to the dosage surface in order to gain a coat with enough thickness for sufficient protection, gastric resistance or proper controlled release.

Adversely for this technique, the wetting force is the only force for adhering the particles onto the dosage surface, and only the wetted particles could adhere onto the dosage surface. As a result, excessive plasticizer is required to wet sufficient amount of particles and then gain enough coat thickness. However, the excessive plasticizer reduces $T_s$ or $T_g$ of the polymer close to or less than room temperature, leading to a very soft and sticky film, which is a lethal defect of this technique and cannot be accepted by the pharmaceutical coating. Moreover, the weak and non-directional wetting force alone is difficult to give a uniform and smooth coating surface.

Another prior-art dry coating technique, here referred to as "electrostatic-dry-coating", is derived from the successfully and widely used electrostatic coating technique in metal finishing.

There are two electrostatic coating processes for the metal finishing industry: electrostatic spraying and electrostatic fluidized bed coating, among which electrostatic spraying is the most common process used for application of powder coatings in metal finishing.

The basic principle of electrostatic spraying concerns propulsion of the dry powder by means of compressed air through a spray gun, in which it becomes electrically charged and then moves and adheres to the earthed substrate surface. The movement of the particles between the charging gun and the substrate is governed by a combination of electrical and hydrodynamic forces. The electrical forces are derived from the repulsion force between the charged particles and the electrostatic attraction between the charged particles and earthed substrate, while the hydrodynamic forces are produced by the air that blows the powder towards the substrate from the spray gun.

The following describes the steps for the charged powder particles to adhere to the substrate surface. First, charged particles are uniformly sprayed onto the earthed substrate by virtue of hydrodynamic forces and electrostatic attractions. As the spraying proceeds, the charged particles attracted onto the substrate surface repel each other due to carrying the same charges, which advantageously induces a uniform and even distribution of particles on the substrate surface, hence producing a uniform coating. When there are enough particles accumulated on the substrate that the repulsion force of the deposited particles against the coming particles reaches and exceeds the electrostatic attraction of the earthed substrate to the coming particles, particles cannot adhere to the substrate any more. At this point, the coating thickness can hardly increase any more, which provides an approach for controlling the coating thickness.

Therefore a successful electrostatic spraying should satisfy several requirements: a powder charging/dispensing unit, an earthed conductive substrate and powdered particles able to be charged.

There are two types of spraying units, generally in the form of guns, classified into corona charging guns and tribo charging guns according to their charging mechanism. Corona charging guns are characterized by electrical breakdown and thereafter ionization of air by imposing a high voltage on a sharp pointed needle-like electrode in the gun, the powder particles picking up the negative ions on their way from the gun to the substrate. Tribo charging guns make use of the principle of frictional charging associated with the electrical properties of solid materials.

Electrostatic coating of solid dosage forms with powdered materials, i.e. electrostatic-dry-coating, is more difficult than coating of metals due to the much weaker electrical conductivity of solid dosage forms than metal substrates. For metal substrates, the sufficiently strong electrostatic attraction between the charged particles and the grounded metal substrate can cause particles to firmly adhere to the substrate surface, producing a coat with a desirable thickness. For solid dosage forms, however, the electrostatic attraction between the charged particles and the solid dosages with weak conductivity or high electric resistance is typically weak, leading to difficulty in producing a thick coat. Despite this difficulty, the more uniform coating produced by electrostatic coating in comparison with the "plasticizer-dry-coating" has been encouraging researchers to devote efforts to overcome this difficulty of the electrostatic-dry-coating. Most of such efforts are exclusively directed to designing special apparatus to fulfill coating solid dosage forms by electrostatic-dry-coating.

US 2003/0138487 A1 (Continuation of U.S. Ser. No. 08/966,582, or PCT/GB96/01101), US 2002/0034592 A1 (Continuation of U.S. Ser. No. 09/629,439), and US 2002/0197388 A1 (Continuation of U.S. Ser. No. 09/310,741) provide an apparatus for electrostatically coating pharmaceutical tablets with powdered coating materials. The apparatus includes two occluding rotary drums, two electrostatic spray guns, two infrared ray-based fusion stations, two cooling stations, a tablet feeding chute and a tablet collection chute (shown in FIG. 1). The special design aims at increasing the electrostatic attraction between the particles and tablets by making every tablet effectively grounded, and at greatly improving the coating efficiency by directing and restricting the charged particles onto the tablet surface without spraying onto the surroundings. However, the apparatus is far from being commercially applicable because it is too complicated thereby leading to operational complications, and completely different from the conventional coating apparatus such as pan coaters and fluidized beds used in liquid coating. Moreover, in order to speed up the coating process, a high fusion temperature (or curing temperature) of above 130° C. or even up to 250° C. seems indispensable since no plasticizer is used in this technique, which may cause a great harm to the coating material as well as the active ingredients, especially for the case where the coating material contains active ingredients.

US 2003/0211229 A1 describes another apparatus based on a photoconductive drum, by which charged powder material is applied to a photoconductive drum, transferred to an intermediate belt and then to a solid dosage form.

All the above mentioned publications on electrostatic-dry-coating focus on new apparatus designs for effective coating of powdered materials on tablets but not making use of the existing apparatus, attempting to improve the electrostatic attractions and thereafter the coating efficiency.

Unfortunately, the increased coating efficiency has been compromised by the complicated coating apparatus, which does little good in cost efficiency to pharmaceutical factories that prefer to accept dry coating operated in a simpler coating apparatus or in their present apparatus such as pan coaters for liquid coating of tablets with few modifications. In addition, all those work focused on tablet coating. No work has been reported on the dry coating of smaller dosage forms such as beads. Those beads are currently coated by liquid spraying in fluidized bed which requires even more hot air to fluidize the particles than a liquid coating pan coater.

The high curing temperatures needed for curing are known to damage the active ingredient in the dosages or coating materials such as those disclosed in US 2003/0138487 A1 (Continuation of U.S. Ser. No. 08/966,582, or PCT/GB96/01101), US 2002/0034592 A1 (Continuation of U.S. Ser. No. 09/629,439), and US 2002/0197388 A1 (Continuation of U.S. Ser. No. 09/310,741) and which may produce fragile coats.

The third dry coating technique was reported most recently by Cerea M et al (Cerea M, Zheng W, Young C, et al. "A novel powder coating process for attaining taste masking and moisture protective films applied to tablets", International J Pharmaceutics 2004, 279:127-139). In this reported technique, only heat was used to realize the dry coating of tablets, so that it may be referred to as "heat-dry-coating". In this coating technique, Eudragit E PO (a copolymer based on dimethylaminoethyl methacrylate and methacrylates) particles were continuously spread onto the tablets contained in a lab-scale spheronizer by way of a motorized single screw powder feeder, with an infrared lamp positioned on the top of the spheronizer as a heating source, without using any solvent and plasticizer (see FIG. 2). Powder adhesion onto the tablet surface is promoted only by the partially melted polymer that generates binding forces between the particles and between the particles and tablet surfaces. Because Eudragit E PO has a low $T_g$ of about 50C and because the film of Eudragit E is sufficiently elastic, coating with Eudragit E generally requires no plasticizers.

However, for the above reported "heat-dry-coating", the coating material used, Eudragit E, is a special example, which does not require plasticizer, so that this coating process does not apply to those polymers requiring plasticizers. In addition, it is also very hard to get a smooth, uniform and thick coating only by the help of the said heat-based adhesion.

Therefore, it would be very advantageous to provide a method and apparatus for direct coating solid dosage forms using powdered materials which overcomes the aforementioned difficulties.

SUMMARY OF THE INVENTION

An objective of the present invention is to provide a method for coating solid dosage forms using powdered materials which avoids the need for organic solvents.

The present invention provides a method of dry coating solid dosage forms, comprising the steps of
method of dry coating solid dosage forms, comprising the steps of:
a) positioning solid dosage forms in a chamber of a rotatable, electrically grounded housing;
b) performing a spraying cycle including spraying a film forming polymer powder composition into the chamber during rotation thereof for a pre-selected length of time using an electrostatic spray gun to form a polymer coating on the solid dosage forms; and
c) curing the coated solid dosage forms to form polymer coated solid dosage forms.

The method may include spraying a suitable amount of dry powdered plasticizer or liquid plasticizer or plasticizer solution (thereafter all called plasticizer) into the housing to coat the solid dosage forms. The suitable amount of plasticizer is enough plasticizer to reduce a $T_g$ of the polymer coating to a range from about 30 to 100° C.

The present invention also provides an apparatus for dry coating solid dosage forms, comprising:
a) a rotatable, electrically grounded housing having an interior chamber for holding solid dosage forms and rotation means for rotating said housing;
b) an electrostatic spray gun for electrostatically spraying a dry film forming polymer powder composition into the chamber for coating the solid dosage forms located in said interior chamber with a dry polymer coating; and
c) an energy source for applying energy to at least partially solidify and bind the dry polymer coating to a surface of the solid dosage forms, thereby forming a continuous uniform polymer coated solid dosage forms.

The apparatus may include an atomizer for spraying additional constituents into the housing for coating solid dosage forms located in said housing with said additional constituents.

A further understanding of the functional and advantageous aspects of the invention can be realized by reference to the following detailed description and drawings.

BRIEF DESCRIPTION OF THE DRAWINGS

The invention will be more fully understood from the following detailed description thereof taken in connection with the accompanying drawings, which form a part of this application, and in which:

FIG. 5 is a diagrammatic representation of yet another alternative pan coater apparatus with an inner plastic shield according to this invention, with FIG. 5b showing the A-A cross-section of FIG. 5a.

DETAILED DESCRIPTION OF THE INVENTION

Figure 1:
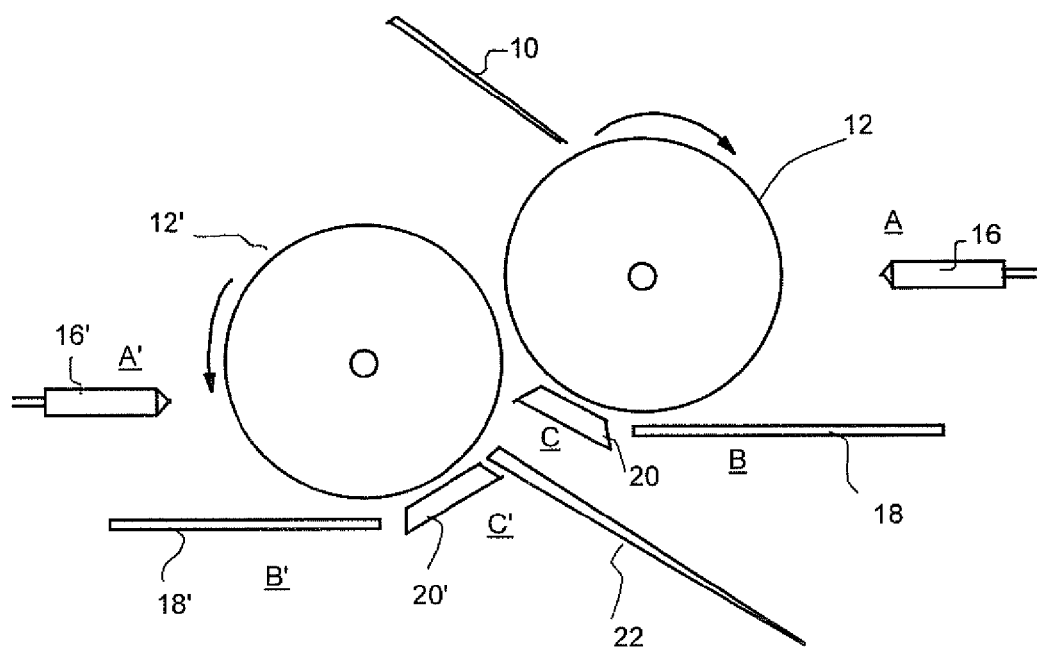
FIG. 1 is a schematic diagram of a Prior-Art electrostatic coating apparatus for solid dosage forms wherein 10: tablet feeding chute; 12, 12': rotary drum; 16, 16': electrostatic spraying gun; 18, 18': tray to hold particles; 20, 20': infrared ray heater; 22: tablet collection chute; A (A'): preconditioning station; B (B'): coating station; C (C'): fusing station. (US 2002/0034592 A1)
Figure 2:
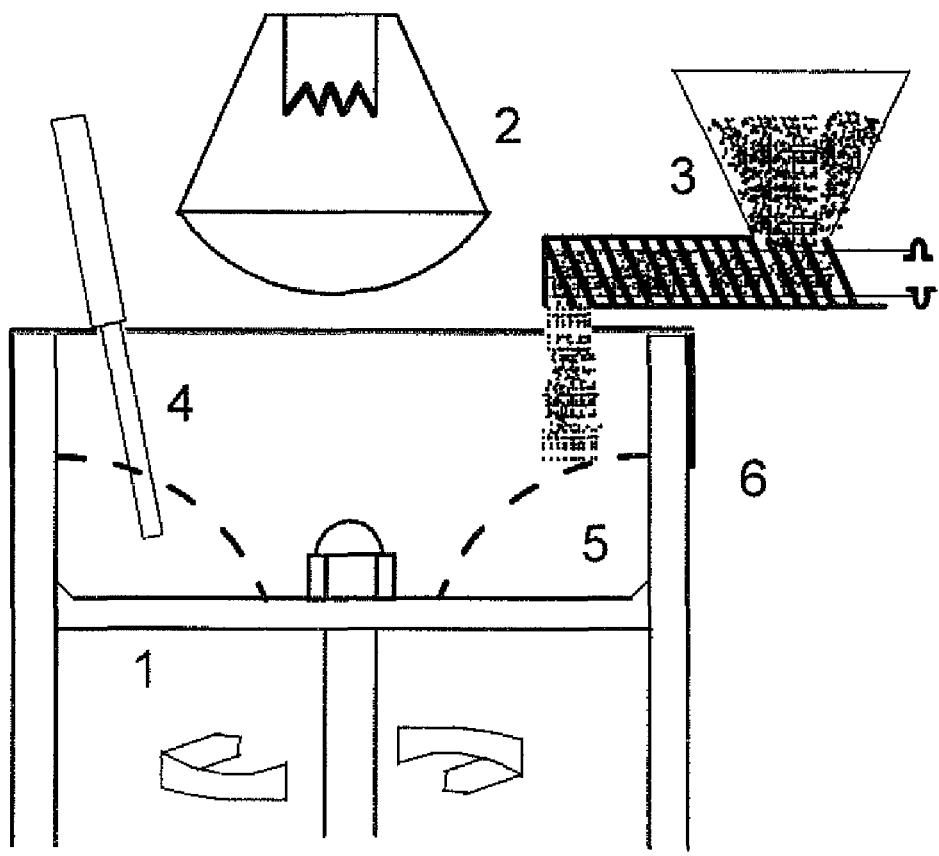
FIG. 2 is a schematic diagram of a Prior-Art heat-dry-coating apparatus and process for tablet coating wherein (1) rotating disk; (2) infrared lamp; (3) powder feeder; (4) temperature probe; (5) coating tablets; (6) glass cover (Cerea M et al)

The phrase "film forming polymer powder composition" refers to the powder polymer being used to form the coating on the solid dosages and can optionally include other constituents or materials. Possible optional materials include fillers such as talc, pigment such as titanium oxide, and small amounts of the solid plasticizer.

As used herein, the term "curing" means applying an energy source, generally a heat source but it may also be an ultraviolet source, to increase the temperature of the coated solid dosage forms, so as to solidify or partially solidify the coating on the surface of the dosage. Such heat source, for example, can be a heating element inside the chamber of the rotatable housing in which the coatings are applied, or outside the housing but close enough to be able to transfer heat to the housing, or a hot air flowing through the chamber. For polymer powders sensitive to ultraviolet waves, an ultraviolet source may also be used as an energy source for curing.

"Dry coating" refers to the film forming polymer powder composition being coated onto the dosages being applied as a dry powder.

Eudragit™ is the trade mark of Rohm GmbH, and Opadry™ is the trade mark of Colorcon.

Taking into consideration of the advantages and disadvantages of the prior-art dry coating techniques, the present inventors have developed a novel dry coating technique which provides all the advantages and overcomes disadvantages of the prior art. In brief, the present invention seeks to provide a dry coating technique with the following features.

According to the present invention, dry coating of all solid dosage forms, such as tablets, pellets, pills, spherules, beads and so on, is carried out in a pan coater similar to the conventional pan coater for liquid coating of tablets with minor modifications. This innovation can make use of the original pan coaters for liquid coating, thus reducing the cost for re-design or avoiding purchase of new complicated equipment as in the prior-art electrostatic-dry-coating and facilitating the commercial application of this technique in the pharmaceutical industry. In addition, it also eliminates the fluidized beds currently used for coating small size solid dosages such as beads, pellets and spherules in liquid coating and plasticizer-dry-coating, which requires a large quantity of compressed air for fluidizing these dosages, adding a large bill for providing and heating compressed gas and post-disposing of the discharged gas.

Without being limited by any theory, five kinds of "forces", including softening or melting effects of particles by heat, wetting of the dosage surface by a plasticizer or plasticizer solution, hydrodynamic force due to spraying, mechanical force due to the rotation of the pan, and electrostatic forces, are combined to enhance the adhesion of powdered coating materials to the solid dosage surface. This then produces, on any solid dosage surface, a uniform, smooth and firm coating with controllable thickness.

As mentioned above, the plasticizer-dry-coating and heat-dry-coating hardly produce a uniform and smooth coating since it is difficult to use electrostatic-dry-coating for control of the coating thickness due to the weak conductivity of solid dosage forms although it can produce relatively more uniform and smooth coating.

According to the present invention, an extremely high coating efficiency of up to 95% can be obtained by using a pan coater rather than a complicated apparatus as in the electrostatic-dry-coating. In the present invention, the pan coater can be made from metals such as stainless steel or plastics. For a plastic coater, a metal insert, such as stainless steel or bronze, is put into the coater, which can wrap around the inner surface of the pan coater. Alternatively, metal nets can be embedded into the plastic pan with some bare metal exposed to the inner side of the pan. The metal coater or the metal part of the plastic coater is grounded so that the dosages contained in the coater are grounded.

Figure 3:
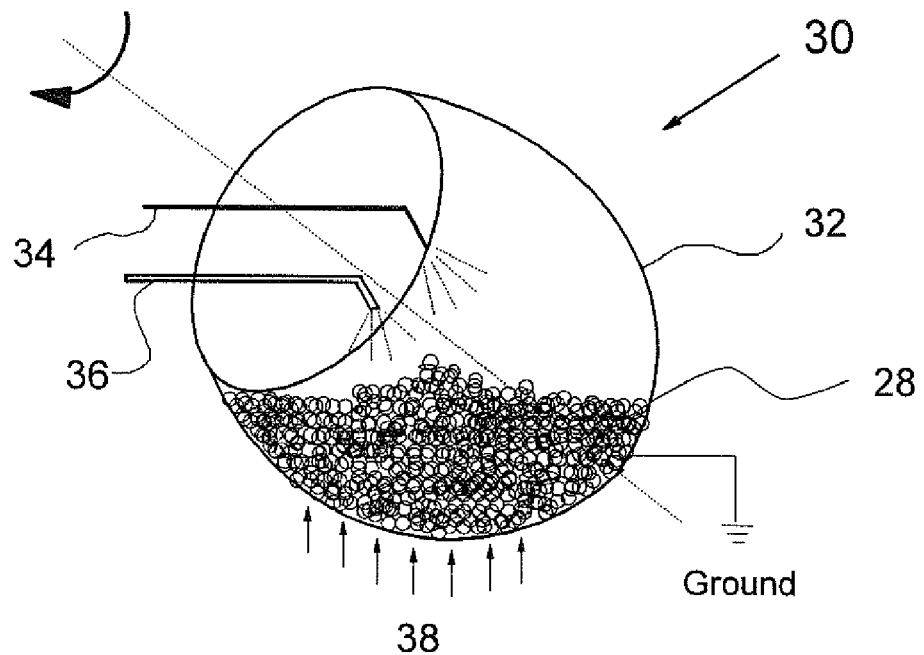
FIG. 3 is a diagrammatic representation of a pan coater apparatus for coating solid dosage forms according to the present invention.

A pan coater according to this invention is shown generally at 30 in FIG. 3. Coating apparatus 30 includes a rotary coater chamber 32 which is electrically grounded and holds the solid dosage forms 28, an atomizer 34 for dispensing the plasticizer, an electrostatic spray gun 36 for dispensing the film forming polymer powder, and a heating source 38 for heating the solid dosage contents in chamber 32. This heating source, although shown at the bottom, can be from any and all directions.

Figure 4:
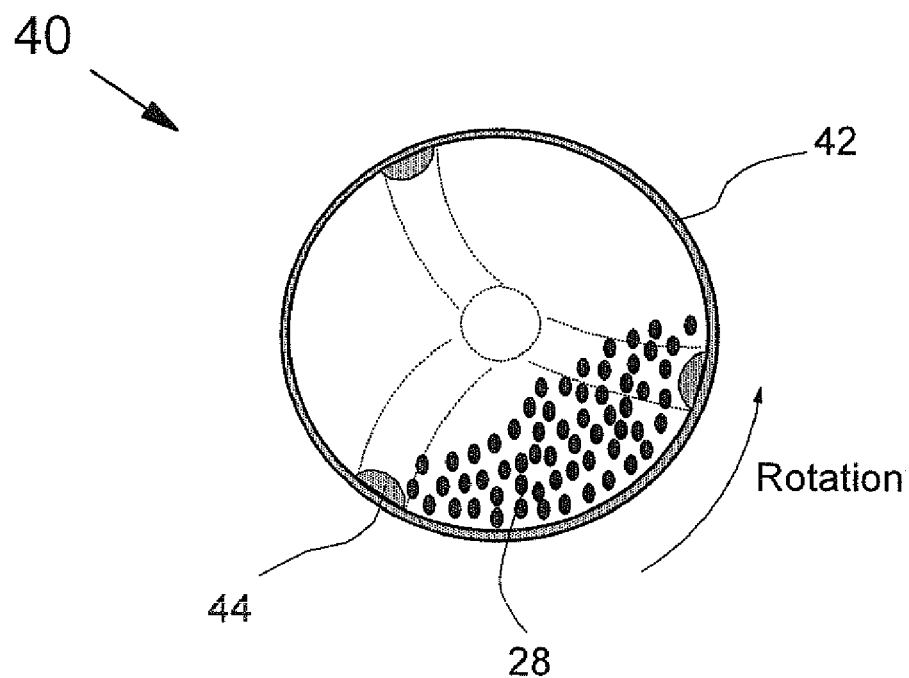
FIG. 4 is a diagrammatic representation (cross-sectional view only) of an alternative pan coater apparatus with agitation protrusions according to this invention.

FIG. 4 shows an alternative pan coater 40, with the addition of multiple protrusions 44 mounted on the pan coater chamber 42, to increase the tumbling of the dosage forms 28. All other features are essentially the same as shown in the embodiment in FIG. 3. The protrusions 44 mounted on the inner surface of the pan coater chamber 42 also increases the tumbling effect, which is beneficial for achieving coating uniformity.

Figure 5A:
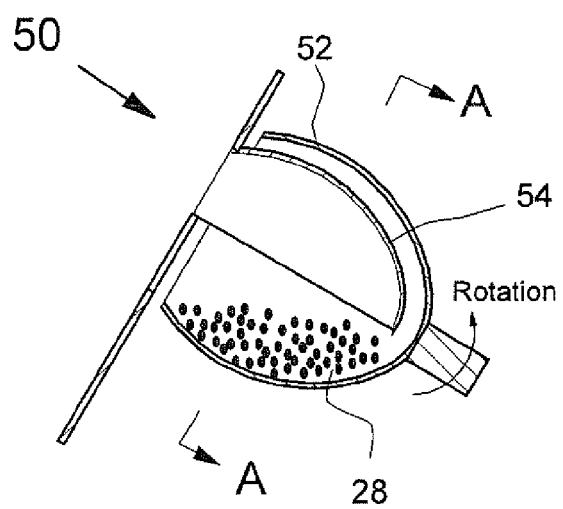
Figure 5B:
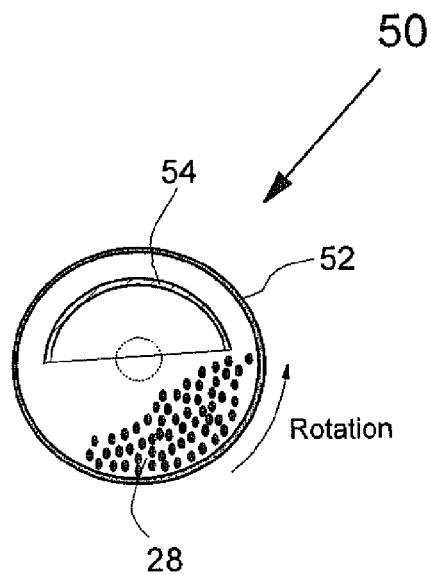

FIG. 5 shows yet another alternative to the pan coater design 50, with a plastic shield 54 installed on the upper portion inside the pan coater chamber 52. This plastic shield is to prevent a significant portion of the charged spraying powder from going to the upper portion of the inner surface of the pan coater chamber.

Figure 6:
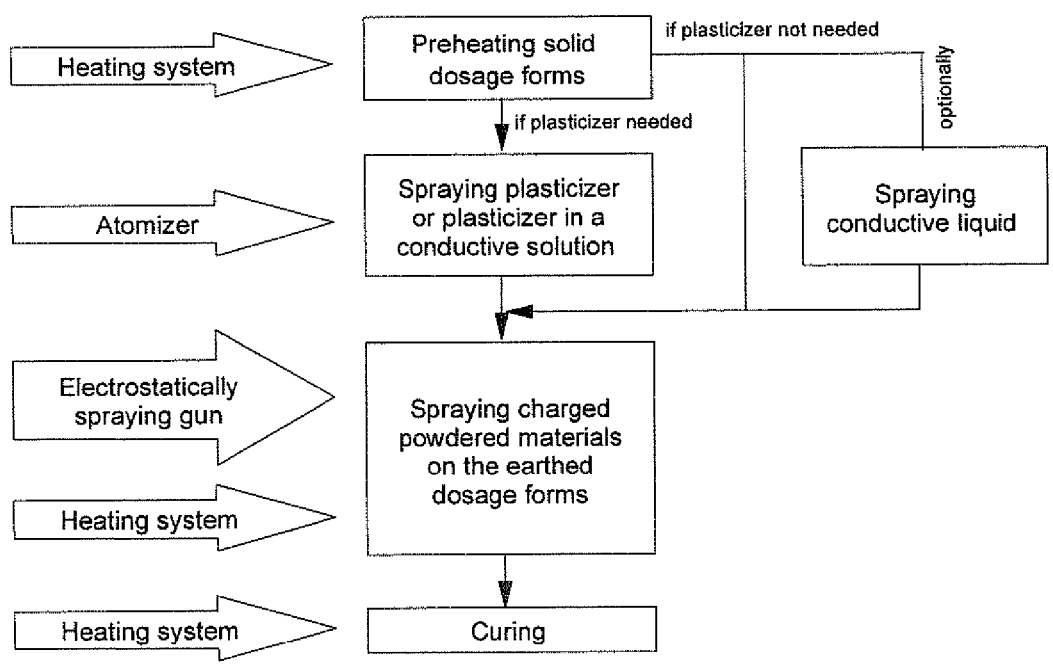
FIG. 6 shows a block diagram of a coating process according to this invention.

FIG. 6 shows a block diagram of the method for the coating process according to this invention. In the present invention, the solid dosages are preferably, although it is not essential, pre-warmed. Then a suitable amount of plasticizer (alone in a powdered or liquid form, or in a form of solution) is sprayed on the preheated dosage surface by means of the atomizer 34. Here "a suitable amount of plasticizer" means enough plasticizer to reduce the $T_g$ of the film-forming polymer to a range from about 30 to about 100° C. depending on the polymer properties, preferably in a range of about 35 to about 80° C., in particular preferably in a range of about 35 to about 60° C. The preheating temperature is close to $T_g$ of the plasticized polymer. Preheating the dosages and then wetting their surfaces with plasticizers greatly strengthen the adhesion of powdered materials on the dosages compared with simply spraying plasticizers without preheating the dosages, because once powdered materials come into contact with the preheated dosages, they become softened or even partially melted, allowing them to more easily adhere to the wetted surface. The wetting also increases the electrical conductivity of the solid dosage, enhancing the electrostatic coating.

The coated solid dosage forms may be cured by heating at a curing temperature ($T_c$) which is in a range from about 5° C. to about 40° C. higher than glass transition temperature ($T_g$) or softening temperature ($T_s$) of the polymer forming the coating.

Sometimes, for those special polymers that are sufficiently elastic with low $T_g$ or $T_s$, such as Eudragit E type polymers, spraying plasticizer is not always necessary. In this case, a separate solution, preferably a conductive solution such as an aqueous salt solution or any non-pure water solution (when impurities are present water is conductive), may be optionally sprayed onto the pre-warmed solid dosages, to increase the wetting and the electrostatic attraction between the powdered materials and the solid dosages.

Subsequently, powdered materials are sprayed through an electrostatic spray unit, generally an electrostatic spray gun by means of compressed air. The spray gun can be a corona charging gun or a tribo charging gun. The plasticizer and film forming powdered polymer materials may be sprayed either simultaneously, or one sprayed first and then the other and the process repeated. That is, if the alternating spray method is used, the spraying cycle (plasticizer spray followed by polymer powder spray) can be repeated until the required thickness is achieved. Preferably, heating continues during the spray of plasticizer/solution and powdered materials. The movement of the powdered materials from the charged gun to the dosages is dominated by a combination of electrical and hydrodynamic forces, and the adhesion of powders onto the dosage surface is the synergic contribution of electrostatic attraction between the charged powders and earthed dosages, softening effects of the powders due to heat from preheating and heating during coating, and wetting effects by plasticizers or solutions if used.

It will be understood that the above described coating process can be repeated if an increased coating thickness is required. That is, after a round of spraying (plasticizer spray together with, or followed by, the polymer powder spray), two or more of these cycles of spraying can be applied to increase the coating thickness. Optionally, in-between the spray cycles, curing may be applied by applying heat for a period time. This process may be repeated until the desired thickness of coating is achieved. In this manner, a greater thickness can be achieved than a single round of spraying.

The spraying of liquid (plasticizer alone, plasticizer solution or just solution) also increases the electro-conductivity at the surface of the solid dosage forms, further enhancing the electrostatic attraction. The hydrodynamic forces from compressed air and the mechanical forces from the tumbling effect of the pan coater are both helpful to the adhesion. Such a synergic mechanism overcomes almost all the disadvantages and possesses all the advantages of the above-mentioned prior-art dry coating techniques, as will be explained in detail in the following description.

Finally the coating may be cured at an elevated temperature in an oven or in the coating chamber 32 where coating is performed, forming a continuous, uniform, smooth and compact coat on the dosage surface. The curing temperature ($T_c$) is dependent on the $T_g$ or $T_s$ of the powdered materials, especially the film-forming polymer. Generally, $T_c$ is 5~40° C. higher, preferably 10~30° C. higher, more preferably 10-20° C. higher than the $T_g$ or $T_s$. The curing time typically varies from half to an hour depending on the difference between $T_c$ and $T_g$. For instance, when the difference is about 10° C., the curing time is about 30 minutes for some of the tests conducted. In this invention, the heat required for preheating, coating and curing is provided by hot air flow, an electric oven, or by other means such as an infrared ray. One aspect that should be clearly emphasized is that, for all solid dosage forms, including tablets, pellets, pills, beads, and spherules, the dry coating process in this invention can be performed in a the devices of FIGS. 3, 4 and 5.

No complicated equipment as required in the prior-art electrostatic-dry-coating is required in the present invention but rather the device of FIGS. 3, 4 and 5 works very well. In addition, the typical fluidized bed coater used in the liquid coating and the prior-art plasticizer-dry-coating for small size solid dosage forms such as pellets, pills, beads and spherules is replaced by the present rotatable housing, so that both the cost resulting from the complicated equipment and the energy needed to provide and heat the large quantity of compressed air for fluidizing these dosages are avoided using the devices of FIGS. 4 to 6. This gives an unparalleled advantage over the liquid coating and the prior-art dry coating techniques.

Another aspect that should be emphasized is that the coating thickness can be regulated in this invention. One way is by regulating the charging voltage. Generally, a higher voltage leads to a thicker coating, but too high a voltage may cause electric breakdown of the coating and damage the coating quality. The voltage can be in a range of 20-120 kV, preferably in a range of 25-70 kV, more preferably in a range of 40-70 kV, and in particular preferably in a range of 50-70 kV. Another way to regulate the coating thickness is by adjusting the amount of plasticizer. Yet another way is to repeat the spraying cycle to increase the coating thickness.

As mentioned before, in the prior-art plasticizer-dry-coating, increasing the coating thickness by increasing the plasticizer feed often leads to a sticky coating. This, however, will not happen with the current invention. Compared with the plasticizer-dry-coating technique, when the same amount of plasticizer is fed, the electrostatic attraction applied in this invented technique helps adhere much more particles to the dosage surface, hence giving a much lower plasticizer/polymer ratio and avoiding a sticky coating. Therefore, in the present invention, a higher amount of plasticizer may give a thicker coating without resulting in a sticky coating which is the case with the plasticizer-dry-coating technique when a higher amount of plasticizer is used.

Another important advantage obtained with the present invention is that a smooth and uniform coating can be achieved in traditional coating equipment, such as the pan coaters for liquid coating, by means of the invented dry coating technique. It has been believed by those skilled in the art that electrostatic powder coating of dosages in a revolving pan coater is to be avoided because the attached particles on the dosage surface by electrostatic attraction may fall off when the dosages tumble in the coater and collide with each other and with the inner surface of the coater. This is only true for a simple electrostatic coating, i.e. the prior art electrostatic-dry-coating, where electrostatic attraction alone is so weak due to the poor conductivity of solid dosages so that it cannot resist the tumbling and colliding. In the present invention, besides the electrostatic attraction, the wetting-induced adhesion force by plasticizer/solution and heat-induced adhesion by preheating, especially the former one, contribute much to enhance the particle adhesion to the dosage surface.

As a result, the adhesion of powdered materials to the dosage surface is so strong that it not only can withstand the tumbling and colliding but the tumbling and colliding actually also help make the coating more compact and uniform. Furthermore, the repulsions between the same charged particles on the dosage surface promote the uniform distribution of the particles on the dosage surface and ensure a uniform coating thickness.

Another aspect that should be pointed out is the particle size of the powdered materials used in this invention. Here the particle size is defined as the volume-mean particle size, as measured by, for example, the Malvern MasterSizer, using a laser light diffraction principle. The particle size has an important effect on the coating quality in a dry coating, especially in an electrostatic based dry coating. Preferably, the powdered materials should have a small particle size, because, firstly a smaller particle has a lighter mass and a larger specific surface area, and secondly a smaller particle could get a higher charging efficiency according to the following equation (Misev T A. Powder coatings: Chemistry and Technology, 1991, Toronto: Wiley, Page 329):

$$\text{Charging efficiency} = (q/m)_{max} = \frac{3\varepsilon_0 E}{(\rho_o)a}\left(1 + 2\frac{\varepsilon_r - 1}{\varepsilon_r + 1}\right).$$

where $\varepsilon_o$=permittivity of free space, $\varepsilon_r$=relative permittivity of powder particles; a=particle radius; $\rho_o$=density of the particle; E=electric field to which the particles are subjected. In addition, a much smoother coating surface can be formed with finer particles.

Consequently, the lighter weight, larger specific surface area and higher charging efficiency increase the electrostatic attractions and reduce the inertial force and the possibility of particles rebounding back off the dosage surface, resulting in an easier and stronger adhesion and evener distribution on the dosage surface. Therefore, the powdered materials used in this invention should have a particle size of less than 100 µm, advantageously less than 60 µm, more advantageously less than 30 µm, most advantageously less than 20 µm. The selection of the particle size should be connected with dosage forms, larger particle sizes are usually acceptable for larger size dosage forms, however, smaller particle sizes are required for smaller size dosage forms, such as beads, pills or pellets, if a smooth coating surface is required. In all cases, finer particles lead to a smoother coating surface if applied properly.

However, powders with particle size less than 25 µm often become sticky and easy to agglomerate, leading to poor flowability and transportability. This is harmful to the formation of a smooth and uniform coating. Such a problem can be overcome as disclosed in U.S. Pat. No. 6,833,185, which disclosed excellent fluidization additives to fine powders, which patent is incorporated herein by reference in its entirety. By utilizing the techniques disclosed in the earlier invention, fine powders can be used for the current invention to produce more uniform coating on the solids dosage forms with very smooth surface.

Again, another aspect worthy of mentioning is the very high coating efficiency of up to 95% observed from this invention. In the said simple prior-art electrostatic-dry-coating, a part of powdered materials is not charged and is not deposited on dosage surface. Some charged powders may even fall off the tumbling dosage surface due to the weak conductivity of dosages. These lead to overspray. The oversprayed powders are damaged and wasted by the input heat during coating (US 2003/0138487 A1, US 2002/0034592 A1). In the present invention, the charged powdered materials are directed onto the dosage surface by the said electrostatic attractions and hydrodynamic forces. Once they adhere to the dosage surface, the heated and wetted surface will enhance the adhesion, while for those uncharged powders, the said hydrodynamic forces, softening effects, wetting effects and tumbling and colliding forces are sufficient to lock the powders on the dosage surface. Therefore, it was observed in our tablet coating experiments that almost all the sprayed powders were directed and attracted onto the tablet surface and no or just little of the sprayed powder attached on the inner surface of the coater, especially then the optional plastic shield shown in FIG. 5 is installed.

Lastly, another much more important advantage of the present invention is the low energy consumption. Within the whole coating and curing process, only a small amount of energy is required to preheat solid dosages and to maintain the temperature during coating, and eventually to raise the temperature to $T_c$ and maintain at $T_c$ until the curing is over. No energy is needed to evaporate solvent, which constitutes the primary source of the heat energy in the liquid coating technique. Furthermore, the short coating time and curing time also considerably reduce the energy consumption.

The present invention is very advantageous in that it provides a method of directly coating solid dosage forms with powdered materials without using any solvent. For all solid dosage forms, the coating process in this invention which also involves electrostatic coating, can be performed in a simple pan coater designed for liquid coating, unlike the prior-art electrostatic-dry-coating process which must be carried out in a much more complicated apparatus that is completely different from those apparatus for liquid coating.

Furthermore, the method disclosed herein eliminates the need for a fluidized bed used in the prior-art plasticizer-dry-coating techniques for small size dosage forms. The simplicity of the coating apparatus which may be used in this invention will facilitate the method being more readily retrofitted into, for example, the pharmaceutical industry. This method also leads to several other advantages, for example the method provides a much more uniform and smoother coating applied to the dosages compared with the prior-art dry coating techniques, such as plasticizer-dry-coating, electrostatic-dry-coating and heat-dry-coating. In addition, very high coating efficiency (nearly 100% utilization of the coating materials in large batch operations) can be achieved using this method.

Hydrodynamic force, mechanical force, electrostatic force, wetting effect of powdered materials and dosage surface by plasticizers or solution and softening or melting effect by heat are synergically combined in this invention for the first time, substantially enhancing the adhesion and uniform distribution of powders on the dosage surface.

The coating thickness or coating level can be regulated in a wide range in this invention through changing the charging voltage or plasticizer feed rate and quantity without causing other problems such as a sticky coat. On the other hand, for the prior-art plasticizer-dry-coating techniques, while a thicker coat can be obtained through increasing plasticizer feed, but the thicker coating is often sticky. The heat-dry-coating almost has no ability to change the coat thickness.

Much shorter processing time is needed in this invention than traditional liquid coating because no solvent is used in this technique.

The dry coating technique of the present invention is highly energy efficient since no solvent vaporization is required and since the processing time is greatly shortened.

The overall operation cost of the dry coating technique disclosed herein is significantly reduced as a result of a high coating efficiency, short processing time, low energy consumption, simple coating equipment and excellent coating quality achieved in this invention, which is incomparable with liquid coating and any of the prior-art dry coating techniques. Environmental friendliness and operation safety are another two advantages compared with liquid coating.

The present method has utility in the pharmaceutical field. This technique possesses all advantages of powder coating due to elimination of solvents, including energy and time saving, environmental friendliness and safety, and because this technique uses similar equipment to that used for liquid coating, it will be relatively inexpensive to retrofit coating equipment to switch from liquid coating to the present dry coating process. The present method may be used to coat all solid dosage forms, such as tablets, pellets, beads, spherules, pills and so on for any purposes, including controlled release, protection, aesthetics and masking.

The present method may also be used in the food preparation industry to coat confectionery with sugar, chocolate or other substances. It may also be used in any other areas where an electrically non-conductive or weakly conductive solid substrate needs to be coated.

As used herein, the terms "comprises", "comprising", "including" and "includes" are to be construed as being inclusive and open ended, and not exclusive. Specifically, when used in this specification including claims, the terms "comprises", "comprising", "including" and "includes" and variations thereof mean the specified features, steps or components are included. These terms are not to be interpreted to exclude the presence of other features, steps or components.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. An apparatus for dry coating solid dosage forms, comprising:
   a) a rotatable, electrically grounded housing having an interior chamber for holding solid dosage forms, rotation means for rotating said housing, and a shield inside said interior chamber;
   b) an electrostatic spray gun for electrostatically spraying a dry film forming polymer powder composition into the chamber for coating the solid dosage forms located in said interior chamber with a dry polymer coating; and
   c) an energy source for applying energy to at least partially solidify and bind the dry polymer coating to a surface of the solid dosage forms, thereby forming a continuous uniform polymer coated solid dosage forms,
   wherein said shield is configured to shield an upper portion of the inner surface of said housing from being coated by the charged spraying powder as said housing rotates.

2. The apparatus according to claim 1 including an atomizer for spraying additional constituents into the chamber for coating the solid dosage forms located in said housing with said additional constituents.

3. The apparatus according to claim 2 wherein said additional constituents include compositions containing a plasticizer.

4. The apparatus according to claim 1 wherein the rotatable, electrically grounded housing includes at least one protrusion mounted to an interior surface of said chamber for increasing a tumbling effect of the solid dosage forms.

5. The apparatus according to claim 1 wherein said shield is plastic.

6. The apparatus according to claim 1 wherein the electrostatic spray gun is a corona discharge gun or a tribo charging gun.

7. The apparatus according to claim 6 including a source of compressed gas used for discharging the powder composition through the corona discharge gun or tribo charging gun.

8. The apparatus according to claim 1 wherein said energy source is a heat source emitting heat to cure the polymer.

9. The apparatus according to claim 1 wherein said energy source is a light source emitting ultraviolet light to positioned to irradiate the coated solid dosages to cure the polymer.

10. An apparatus for dry coating solid dosage forms, comprising:
    a) a rotatable housing including a chamber for holding solid dosage forms, rotation means for rotating said housing, said chamber having
       i) at least one protrusion mounted to an interior surface of said chamber for increasing a tumbling effect of the solid dosage forms,
       ii) a first portion of said interior surface that is electrically grounded,
       iii) a second portion of said interior surface that is not electrically grounded;
    b) an electrostatic spray gun for electrostatically spraying a dry film forming polymer powder composition into said chamber for coating the solid dosage forms located in said chamber with a dry polymer coating; and
    c) an energy source for applying energy to at least partially solidify and bind the dry polymer coating to a surface of the solid dosage forms, thereby forming continuous uniform polymer coated solid dosage forms
    wherein said chamber is formed from a plastic material having at least one metal insert embedded therein so said first portion of said interior is metal and said second portion of said interior is plastic,
    wherein said at least one metal insert is a metal net.

11. The apparatus according to claim 10 including an atomizer for spraying additional constituents into the chamber for coating the solid dosage forms located in said housing with said additional constituents.

12. The apparatus according to claim 10 wherein the electrostatic spray gun is one of a corona discharge gun and a tribo charging gun.

13. The apparatus according to claim 10 wherein said energy source is a heat source emitting heat to cure the polymer.

14. The apparatus according to claim 10 wherein said energy source is a light source emitting ultraviolet light to positioned to irradiate the coated solid dosages to cure the polymer.

15. An apparatus for dry coating solid dosage forms, comprising:
    a) a rotatable housing including a chamber for holding solid dosage forms and rotation means for rotating said housing, said chamber being formed of a plastic material having at least one metal insert that is electrically grounded;
    b) an electrostatic spray gun for electrostatically spraying a dry film forming polymer powder composition into said chamber for coating the solid dosage forms located in said chamber with a dry polymer coating; and
    c) an energy source for applying energy to at least partially solidify and bind the dry polymer coating to a surface of the solid dosage forms, thereby forming a continuous uniform polymer coated solid dosage forms wherein said at least one metal insert is a metal net
    wherein the rotatable housing includes a shield inside said chamber for shielding an upper portion of the inner surface of the housing from being coated by the charged spraying powder as said housing rotates.

16. The apparatus according to claim 15 including an atomizer for spraying additional constituents into the chamber for coating the solid dosage forms located in said housing with said additional constituents.

17. The apparatus according to claim 15 wherein the electrostatic spray gun is one of a corona discharge gun and a tribo charging gun.

18. The apparatus according to claim 15 wherein said energy source is a heat source emitting heat to cure the polymer.

19. The apparatus according to claim 15 wherein said energy source is a light source emitting ultraviolet light to positioned to irradiate the coated solid dosages to cure the polymer.

20. The apparatus according to claim 15 wherein the rotatable housing includes at least one protrusion mounted to an interior surface of said chamber for increasing a tumbling effect of the solid dosage forms.

21. An apparatus for dry coating solid dosage forms, comprising:
  a) a rotatable housing including a chamber for holding solid dosage forms, rotation means for rotating said housing, said chamber having
    i) at least one protrusion mounted to an interior surface of said chamber for increasing a tumbling effect of the solid dosage forms,
    ii) a first portion of said interior surface that is electrically grounded,
    iii) a second portion of said interior surface that is not electrically grounded;
  b) an electrostatic spray gun for electrostatically spraying a dry film forming polymer powder composition into said chamber for coating the solid dosage forms located in said chamber with a dry polymer coating; and
  c) an energy source for applying energy to at least partially solidify and bind the dry polymer coating to the solid dosage forms, thereby forming continuous uniform polymer coated solid dosage forms.

22. An apparatus for dry coating solid dosage forms, comprising:
  a) a rotatable housing including a chamber for holding solid dosage forms and rotation means for rotating said housing, said chamber being formed of a plastic material having at least one metal insert that is electrically grounded;
  b) an electrostatic spray gun for electrostatically spraying a dry film forming polymer powder composition into said chamber for coating the solid dosage forms located in said chamber with a dry polymer coating; and
  c) an energy source for applying energy to at least partially solidify and bind the dry polymer coating to the surface of the solid dosage forms, thereby forming continuous uniform polymer coated solid dosage forms,
  wherein said at least one metal insert is a metal net.

* * * * *